US009801836B2

(12) United States Patent
Della Valle et al.

(10) Patent No.: US 9,801,836 B2
(45) Date of Patent: Oct. 31, 2017

(54) USING PALMITOYLETHANOLAMIDE IN COMBINATION WITH OPIOIDS

(71) Applicant: Epitech Group S.r.l., Milan (IT)

(72) Inventors: Francesco Della Valle, Milan (IT); Maria Federica Della Valle, Milan (IT); Lorenzo Di Cesare Manelli, Milan (IT); Carla Ghelardini, Milan (IT)

(73) Assignee: Epitech Group S.r.l., Milan (IT)

( * ) Notice: Subject to any disclaimer, the term of this patent is extended or adjusted under 35 U.S.C. 154(b) by 0 days.

(21) Appl. No.: 14/711,112

(22) Filed: May 13, 2015

(65) Prior Publication Data
US 2015/0328173 A1 Nov. 19, 2015

(30) Foreign Application Priority Data

May 14, 2014 (IT) .............. MI2014A0876

(51) Int. Cl.
*A61K 31/164* (2006.01)
*A61K 9/14* (2006.01)
*A61K 31/4468* (2006.01)
*A61K 31/485* (2006.01)
*A61K 45/06* (2006.01)

(52) U.S. Cl.
CPC .............. *A61K 31/164* (2013.01); *A61K 9/14* (2013.01); *A61K 31/4468* (2013.01); *A61K 31/485* (2013.01); *A61K 45/06* (2013.01)

(58) Field of Classification Search
None
See application file for complete search history.

(56) References Cited

U.S. PATENT DOCUMENTS

2011/0171313 A1* 7/2011 Della Valle .......... A61K 9/0056
424/489

FOREIGN PATENT DOCUMENTS

WO WO-2005-107726 * 11/2005

OTHER PUBLICATIONS

DuPen A, Mechanims of opioid-induced tolerance and hyperalgesia, Pain Manag Nurs, 2007, 8(3), 113-121.*
Dominguez et al., "N-palmitoylethanolamide in the treatment of neuropathic pain associated with lumbosciatica", Pain Management, 2012, vol. 2, No. 2, pp. 119-124.
Gatti et al., "Palmitoylethanolamide in the Treatment of Chronic Pain Caused by Different Etiopathogenesis", Pain Medicine, 2012, vol. 13, pp. 1121-1130.
Haller et al., "Non-cannabinoid CB1, non-cannabinoid CB2 antinociceptive effects of several novel compounds in the PPQ stretch test in mice", European Journal of Pharmacology, 2006, vol. 546, pp. 60-68.
Skaper et al., "Palmitoylethanolamide, a naturally occurring disease-modifying agent in neuropathic pain", Inflammopharmacology, 2014, vol. 22, pp. 79-94.
Italian Search Report, Application No. IT MI20140876 dated Jan. 19, 2015.
Italian Written Opinion, Application No. IT MI20140876 dated Jan. 19, 2015.

* cited by examiner

*Primary Examiner* — Celeste A Roney
(74) *Attorney, Agent, or Firm* — MacMillan, Sobanski & Todd, LLC

(57) ABSTRACT

Described herein are pharmaceutical compositions for human or animal use containing N-palmitoylethanolamide as an analgesic in combination with opioids. In particular, the compositions include palmitoylethanolamide in non-micronized form, in micronized form (PEA-m), in ultra-micronized form (PEAum) or mixtures thereof, for use in humans or animals in combination with an opioid in the treatment of pain conditions, wherein said palmitoylethanolamide is administered separately, sequentially, or in combination with said opioid.

6 Claims, 1 Drawing Sheet

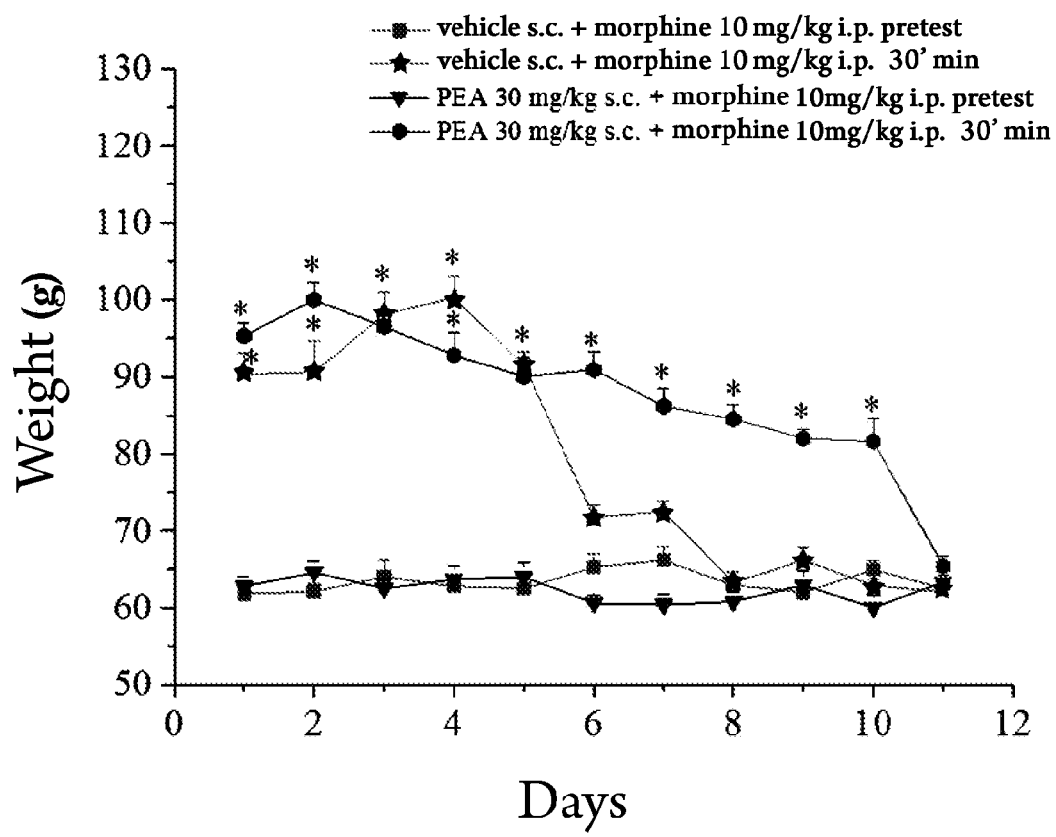

USING PALMITOYLETHANOLAMIDE IN COMBINATION WITH OPIOIDS

CROSS-REFERENCE TO RELATED APPLICATIONS

This application claims the priority to Italian Application Number MI2014A000876 filed May 14, 2014, the entire disclosures of which are expressly incorporated herein by reference.

DESCRIPTION

Field of the Technique of the Invention

This invention relates to a pharmaceutical composition for human or animal use containing N-palmitoylethanolamide as an analgesic in combination with opioids.

State of the Art

Opioids are substances active on the opioid receptor and having an analgesic action. They include both natural alkaloids such as morphine and its analogues (also called opiates, since derived from opium) and synthetic or semi-synthetic compounds with an alkaloid (heroin) or non-alkaloid (methadone) structure.

Morphine, the principal natural alkaloid extracted from *Papaver somniferum*, is the therapeutic treatment of choice for the control of moderate and severe pain. Despite the power and efficacy of morphine, the application of the substance in the continuous therapy of persistent pain is limited by the development of tolerance to the analgesic effect. The development of tolerance requires continuous dose increases to achieve the same analgesic effect. This complex pathophysiological cycle helps to decrease the quality of life of patients due to excessive sedation, reduced physical activity, constipation, respiratory depression, etc.

There is extensive literature describing the establishment of this phenomenon in experimental animals. Several hypotheses have been advanced to explain the tolerance to opioids. The mechanisms considered include: the reduction of coupling between the opioid receptor and the G protein with loss of the ability to exchange GDP with GTP, desensitization and receptor down-regulation with internalization of the activated receptor, receptorial internalization and dimerization of the $\mu$ receptor.

In particular, there is recent evidence of the involvement of spinal glial cells during development of tolerance. It is demonstrated that there is an activation of microglia and astrocyte cells at the development of analgesic tolerance to morphine and other opioids. It has also been suggested that an inhibition of these cell types is able to delay the analgesic efficacy of opioids.

Palmitoylethanolamide (PEA) is an endogenous amide formed from palmitic acid and ethanolamine. It is a lipidic mediator known to exert antinociceptive effects against different types of pain and is characterized by an interesting antineuropathic profile, especially when used in a micronized or ultra-micronized form.

SUMMARY OF THE INVENTION

The inventors of this patent have surprisingly discovered that PEA has the ability to significantly reduce the activation of glial cells in the spinal cord and brain in pathologies characterized by chronic pain.

We then surprisingly discovered that ultramicronized PEA is able to intervene in the processes of development of tolerance due to the prolonged use of opioids, in particular morphine. The association of PEA to the opioid allows prolonging the efficacy of the treatment providing a duration of the analgesic effect that is double compared to treatment with the opioid administered alone.

An object of this invention is thus palmitoylethanolamide (PEA), alternately in non-micronized form (non-micronized PEA), in micronized form (PEA-m) or in ultra-micronized form (PEA-um), for use in combination with an opioid in the treatment of pain conditions, wherein said palmitoylethanolamide is administered separately, sequentially, or in combination with said opioid.

In particular, the object of this invention is palmitoylethanolamide (PEA), alternately in nonmicronized form (non-micronized PEA), in micronized form (PEA-m) or in ultra-micronized form (PEA-um), or a pharmaceutical composition that includes it, for use in a patient as an analgesic in combination with an opioid, wherein said palmitoylethanolamide retards the development of tolerance to the opioid in the patient.

The invention is defined by the appended claims.

Further characteristics and advantages of the process according to the invention will be evident from the following description of examples of preferred embodiments, provided in an indicative and non-limiting way.

BRIEF DESCRIPTION OF THE FIGURES

FIG. 1 shows a graph relating to a "paw pressure" test on rats using morphine alone or morphine in combination with PEA.

DETAILED DESCRIPTION OF THE INVENTION

The invention relates to palmitoylethanolamide (PEA), alternatively in non-micronized form (nonmicronized PEA), in micronized form (PEA-m), in ultramicronized form (PEA-um) or mixtures thereof, for use in humans or animals in combination with an opioid in the treatment of pain conditions, wherein said palmitoylethanolamide is administered separately, sequentially, or in combination with said opioid.

In particular, the invention relates to palmitoylethanolamide (PEA), alternately in nonmicronized form (non-micronized PEA), in micronized form (PEA-m), in ultra-micronized form (PEA-um), mixtures thereof, or a pharmaceutical composition that includes it, for use in a patient as an analgesic in combination with an opioid, wherein said palmitoylethanolamide retards the development of tolerance to the opioid in the patient.

Palmitoylethanolamide can be synthesized as described in example no. 25 of patent U.S. Pat. No. 5,990,170.

Non-micronized PEA can be obtained by finely grinding the product obtained from synthesis; one can obtain a product with particle size between 50.0 and 100.0 $\mu$m. PEA-m can be obtained as described in U.S. Pat. No. 6,548,550 B1 and has a particle size of between 2.0 and 10.0 $\mu$m.

PEA-um can be obtained as described in PCT application no. WO 2011/027373 A1 and has a particle size of between 0.8 and 6.0 $\mu$m.

More information on these forms of PEA are present in the patent publications referred to above, whose contents related to the characterization of the product is incorporated herein by reference.

The opioid is selected from natural alkaloids, also called opiates or compounds of synthesis or semisynthesis.

Preferably, the opioid is selected from: morphine, heroin, etorphine, hydromorphone, oxymorphone, levorphanol, codeine, hydrocodone, oxycodone, nalmefene, nalorphine, naloxone, naltrexone, buprenorphine, butorphanol, nalbuphine, methylnaltrexone, fentanyl and methadone.

More preferably, the opioid is morphine.

The opioids can be administered in humans by means of the various traditional routes of administration in accordance with the instructions contained in Goodman and Gilman's "The Pharmacological Basis of Therapeutics" 12th edition—Chapter 18, Table 18-2, page 498.

Palmitoylethanolamide can be administered in humans starting from 1 day before the start of the treatment with the opioid, or if necessary, by carrying out a 10-day pretreatment before the start of treatment with the opioid.

The range of daily dose of Palmitoylethanolamide is between 3 and 50 mg/kg of patient weight (preferably 20-30 mg/kg) preferably divided into two daily treatments spaced 8-10 hours apart. The daily treatment with palmitoylethanolamide has to be maintained during the entire period of treatment with the opioid. It must be considered that it may be necessary to make continuous changes in the dosage depending on the age and weight of the patient and even the severity of the medical condition being treated. The exact dose and route of administration will ultimately be at the discretion of the attending physician or veterinarian.

The treatment with palmitoylethanolamide is administered orally, sublingually or rectally in the pharmaceutical forms of tablets, hard gelatine capsules, soft gelatine capsules in an oily vehicle, granulate for sublingual use, emulsion for oral use, effervescent tablets, suppositories, or microenemas.

The inventive composition may thus contain pharmaceutically acceptable excipients and additives, selected as a function of the pharmaceutical form chosen.

For oral administration, the pharmaceutical compositions may contain pharmaceutically acceptable excipients such as binding agents (for example pregelatinised corn starch, polyvinylpyrrolidone or hydroxypropyl methylcellulose); filling agents (for example lactose, microcrystalline cellulose or calcium hydrogen phosphate); lubricants (for example magnesium stearate, talc or silica); disintegrants (for example potato starch or sodium starch glycolate); or inhibiting agents (for example sodium lauryl sulphate). The tablets may be coated by methods well known in the art. The liquid preparations for oral administration can present themselves, for example, in the forms of solutions, syrups or suspensions or can be presented as freezedried products to be reconstituted before use with water or other suitable vehicles. Such liquid preparations may be prepared by conventional methods with pharmaceutically acceptable additives such as suspending agents (for example sorbitol syrup, cellulose derivatives or edible hydrogenated fats); emulsifying agents (for example lecithin or acacia); non-aqueous vehicles (for example almond oil, oily esters, ethyl alcohol or fractionated vegetable oils); and preservatives (for example methyl- or propyl-p hydroxybenzoates or sorbic acid). The preparation may also appropriately contain flavourings, colourings and sweetening agents.

The preparations for oral administration may be formulated in a manner suitable to allow the controlled release of the active ingredient.

For buccal administration, the compositions may be in the form of tablets or lozenges formulated in a conventional manner, suitable for absorption in the buccal mucosa. Typical buccal formulations are tablets for sublingual administration.

According to this invention, the compounds may also be formulated according rectal compositions such as suppositories, retention enemas or micro-enemas, for example containing the basic components of common suppositories such as cocoa butter or other glycerides.

In addition to the compositions described previously, the compounds may also be formulated as deposit preparations. Such long-acting formulations can be administered by implantation (for example in a subcutaneous, transcutaneous or intramuscular manner) or by intramuscular injection. So, for example, the compounds according to this invention, can be formulated with suitable polymeric or hydrophobic materials (for example in the form of an emulsion in a suitable oil), ion exchange resins, or as minimally soluble derivatives such as, for example, minimally soluble salt.

The formulations described above can be prepared according to conventional methods, such as those described in Remington's Pharmaceutical Sciences Handbook, Mack Pub. Co., NY, USA.

EXPERIMENTAL PART

With the objective of evaluating the effect of PEA on the phenomena of tolerance to opioids, the development of tolerance to morphine has been reproduced in an animal model. Chronic treatment with said opioid was accompanied by co-administration with ultramicronized PEA suspended in vehicle (consisting of aqueous solution of Pluronic F-68) in order to evaluate the ability of the substance in question to delay the development of tolerance.

Two groups of animals were treated daily subcutaneously (s.c.) with vehicle only or with ultramicronized PEA (PEAum, 30 mg/kg) suspended in the vehicle as indicated above. Starting from day 1, and then in the following days, morphine was administered (10 mg/kg i.p.). As shown in FIG. 1, the painful threshold was measured before injection of morphine (pretest) and 30 minutes after.

The behavioural assessments were made using the "Paw Pressure" test (Ugo Basile, Paw Pressure Analgesy Meter "Randar-Selitto" Rat) evaluating the weight supported by the animal on the hind leg. The rats treated with vehicle+morphine showed a significant increase of the pain threshold compared to the pretest up to the 5th day of treatment, when they developed tolerance that did not allow the detection of further analgesic effects.

In contrast, the group of animals treated with PEAum+morphine showed a prolongation of the analgesic effect that was significant up to the 10th day.

On the other hand, no significant difference emerged in the efficacy of the analgesic effect of the morphine between the two groups.

In conclusion, we surprisingly discovered that ultra-micronized PEA is able to intervene in the processes of development of tolerance due to the prolonged use of opioids, exemplified in the present model by morphine. The association of PEA to the opioid allows prolonging the efficacy of the treatment providing a duration of the analgesic effect that is double compared to treatment with the opioid administered alone.

Results similar to those obtained in experiments with morphine can be achieved with the principal opioid substances normally used in therapy, such as those listed above.

The invention claimed is:

1. A method of delaying the onset of opioid tolerance in a patient under treatment of pain conditions with morphine, comprising administering an effective amount of palmitoylethanolamide ultra-micronized form (PEAum), wherein said palmitoylethanolamide is administered daily to the patient starting from 1 day before the start of treatment with morphine, or carrying out a 10-day pre-treatment before the start of treatment with morphine.

2. The method of claim 1, wherein said ultra-micronized palmitoylethanolamide has a particle size ranging between 0.8 and 6.0 μm.

3. The method of claim 1, wherein a daily dose range of palmitoylethanolamide ranges between 3 and 50 mg/Kg weight of the patient, or 20-30 mg/Kg weight of the patient.

4. The method of claim 1, wherein the administration of palmitoylethanolamide is divided into two daily treatments.

5. The method of claim 1, wherein a daily treatment with palmitoylethanolamide is maintained during the entire period of treatment with the morphine.

6. The method of claim 4, wherein the administration of palmitoylethanolamide is divided into two daily treatments, mutually spaced apart by 8-10 hours.

\* \* \* \* \*

UNITED STATES PATENT AND TRADEMARK OFFICE
CERTIFICATE OF CORRECTION

Page 1 of 1

PATENT NO. : 9,801,836 B2
APPLICATION NO. : 14/711112
DATED : October 31, 2017
INVENTOR(S) : Francesco Della Valle et al.

It is certified that error appears in the above-identified patent and that said Letters Patent is hereby corrected as shown below:

On the Title Page

(30) Foreign Application Priority Data, please correct the priority number from: MI2014A0876" to -- MI2014A000876 --.

In the Claims

Claim 1, Column 4, Line 67, after "palmitoylethanolamide" insert -- in --.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*